United States Patent [19]

Schulz

[11] Patent Number: 5,019,351
[45] Date of Patent: May 28, 1991

[54] AGGLUTINATION REACTION SLIDE

[75] Inventor: Peter Schulz, Pfreimd, Fed. Rep. of Germany

[73] Assignee: Hoffman-La Roche Inc., Nutley, N.J.

[21] Appl. No.: 593,594

[22] Filed: Oct. 9, 1990

Related U.S. Application Data

[63] Continuation of Ser. No. 343,108, Apr. 25, 1989, abandoned.

[30] Foreign Application Priority Data

Apr. 29, 1988 [DE] Fed. Rep. of Germany ....... 3814585

[51] Int. Cl.$^5$ .......................................... G01N 21/03
[52] U.S. Cl. ...................... 422/99; 422/58; 422/73; 422/101; 422/102; 436/178; 356/244; 356/246; 350/536; 73/864.72
[58] Field of Search ........................ 422/55, 58, 72, 73, 422/99, 101, 102; 436/45, 177, 178; 356/244, 246; 350/534, 536; 73/864.02, 864.72

[56] References Cited

U.S. PATENT DOCUMENTS

| | | | |
|---|---|---|---|
| 4,088,448 | 5/1978 | Lilja et al. | 356/246 X |
| 4,271,119 | 6/1981 | Columbus | 422/58 X |
| 4,310,399 | 1/1982 | Columbus | 422/58 X |
| 4,557,600 | 12/1985 | Klose et al. | 436/45 X |
| 4,596,695 | 6/1986 | Cottingham | 422/58 |
| 4,597,944 | 7/1986 | Cottingham | 422/73 |
| 4,654,197 | 3/1987 | Lilja et al. | 422/56 |
| 4,756,884 | 7/1988 | Hillman et al. | 422/73 |
| 4,761,381 | 8/1988 | Blatt et al. | 436/165 |
| 4,775,515 | 10/1988 | Cottingham | 422/101 X |
| 4,806,015 | 3/1989 | Cottingham | 356/335 |

FOREIGN PATENT DOCUMENTS

| | | |
|---|---|---|
| 212314 | 3/1987 | European Pat. Off. . |
| 2325920 | 4/1977 | France . |
| WO89/03992 | 5/1989 | Int'l Pat. Institute . |
| 2168808 | 6/1986 | United Kingdom . |

OTHER PUBLICATIONS

Zentralverband der Elektrotechnischen Industrie e.V., Fügen von Formteilen und Halzeugen aus thermoplastischen Kunststoffen mit Ultraschall, pp. 17–22 (1985).
Blue Print D-682 (Feb. 9, 1987) (confidential information deleted).

Primary Examiner—Robert J. Warden
Assistant Examiner—Lynn M. Kummert
Attorney, Agent, or Firm—George M. Gould; Bernard S. Leon; George W. Johnston

[57] ABSTRACT

A test element for agglutination tests, comprising a receiving and mixing region for a sample and reagents and a reaction capillary having an upstream region which produces a capillary effect causing the sample-reagents mixture to flow at a speed which is greater than along a downstream region of the reaction capillary. An intermediate region can be provided between the upstream capillary region and the downstream region. The downstream end of capillary is connected to a collecting region. The test element is characterized by continuous supply and movement of the sample-reagents mixture through the reaction capillary. More particularly the time needed for a sample-reagents mixture to flow from the upstream end to the downstream end of the reaction capillary fluctuates only slightly between tests. The test element is particularly suitable for detecting drugs of abuse such as cocaine metabolites in human body fluids.

17 Claims, 2 Drawing Sheets

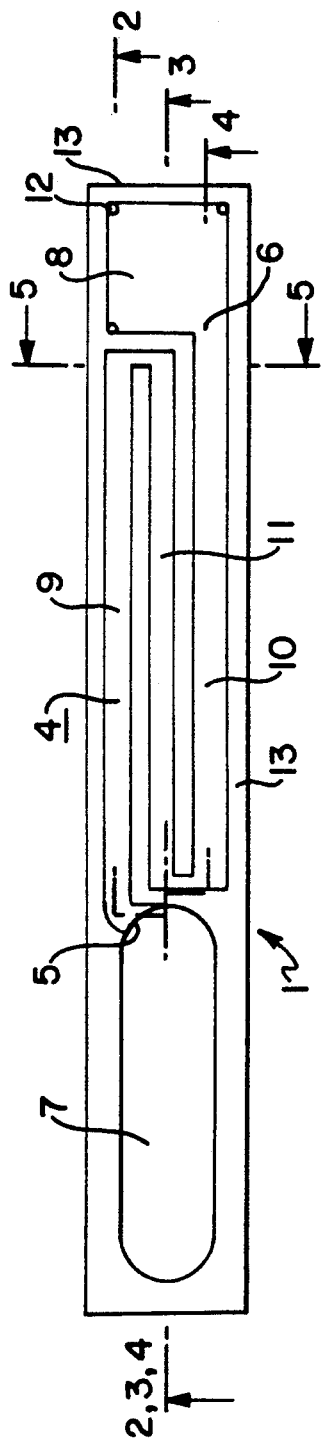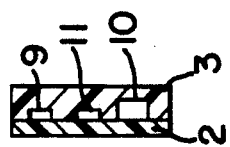

AGGLUTINATION REACTION SLIDE

This application is a continuation of application Ser. No. 07/343,108, filed Apr. 25, 1989, now abandoned.

FIELD OF THE INVENTION

The invention relates to a test element for agglutination tests comprising at least one reaction capillary for a sample-reagents mixture to flow through, the input end of the capillary being connected to a region for receiving and mixing a sample with reagents. The invention relates also to a method of manufacturing the test element, and use thereof for immunological tests.

BACKGROUND

Specific substances under search or to be screened, such as drugs or habit-forming substances hormones, viral, bacterial and parasitic antigens, as well as substances shich could be indicative of specific illnesses (e.g. tumor markers) or the like. can be detected in body fluids such as urine or blood by agglutination reactions. The agglutination occurs in a mixture of an antibody reagent, a reagent comprising a latex coated with a substance under search or metabolite thereof, and the body fluid. The quantity of antibodies in the antibody reagent is limited and they can combine both with the substance under search or metabolite in the latex and with the substance under search in the body fluid. Agglutinations form only if, owing to the absence of the substance under search or metabolite in the body fluid there is a sufficient quantity of antibodies to react with the latex particles. Then, a number of latex particles can agglomerate into visually definable agglutinations. If the substance under search or metabolite is present in the body fluid, there are far fewer antibodies available for agglutination, since the antibodies form an immune complex with the substance under search or metabolite in the body fluid. In that event, the agglutination reaction is very weak or non-existent.

Another type of assay for determining substances of the above-mentioned kind can be carried out by means of agglutination reactions which under certain conditions can take place in a mixture of a reagent comprising a latex coated with an antibody directed against the substance to be determined. In such a mixture visually definable agglutinations form only if there is a sufficient quantity of the substance being sought in the body fluid, whereas no agglutination takes place if the substance being sought is absent in the body fluid under examination. Antibodies in blood or other body fluids can also be determined in a similar way, in which case the corresponding substances or antigens or even also antibodies, which are directed against the substance being sought can be used as agglutination partner in the agglutination system.

In one method of immunological testing of the aforementioned kind, a sample and reagents are poured into a test-tube mixed and kept reacting for some time by shaking and tilting the test-tube by hand. This procedure can result in different agglutination reactions depending on the duration and intensity of shaking and tilting the test-tube. In view of the resulting uncertainty in evaluating the reaction results, it has been suggested (DE-A-35 37 734 and US-A-4,596,695) to conduct the agglutination reaction in a reaction capillary. As a result, there is no need for manually spinning or shaking the sample-reagents mixture, since the movement of the mixture produced by capillary action along the reaction capillary ensures that the sample is mixed with the reagents and that a continuous motion of the sample-reagent mixture takes place for a given time suitable for forming agglutinations.

In this known test device the reaction capillary is disposed between two transparent glass plates which form a capillary chamber by being held at a set constant distance from one another. The capillary action on the respective sample-reagents mixture is therefore substantially constant along the chamber.

Under these conditions, the reaction sensitivity and also the reproducibility of the reaction results are disadvantageously subject to wide fluctuations. This is because, when a given test is performed in different ways, the sample-reagents mixture takes different times to flow through the capillary chamber. Thus, an important criterion for obtaining reproducible results is the maintenance of uniform reaction times. Another condition for optimum sensitivity of the agglutination reaction is that the reaction be given a fixed time to occur (e.g., 3 minutes) with only slight deviations upward or downward.

SUMMARY OF THE INVENTION

The invention concerns an easily-manipulated test element for agglutination reactions which is uncomplicated in construction and economic to manufacture. It also enables an informative agglutination reaction to occur in the respective sample-reagents mixture within a reproducible time without action of external forces such as manual shaking or spinning or by thermal convection.

According to the invention, a test element is configured so that its reaction capillary comprises an upstream region having a capillary action for obtaining a greater flow speed for the sample-reagents mixture than along a downstream region of the reaction capillary. Accordingly in the inventive test element a pumping effect is exerted on the sample-reagents mixture in one region (upstream region) of the reaction capillary, thus ensuring a constant supplY and movement of the mixture in and through the other or downstream region, which therefore can be designed for optimum conditions in forming agglutinations. As described in this application, the sample-reagents mixture flows from upstream to downstream.

Advantageously, the time needed by a sample-reagents mixture to flow from the upstream to the downstream end of the capillary fluctuates only very slightly between different tests for a given fluid in a given size of test element. Therefore, an important precondition for maximum sensitivity of the agglutination reaction is satisfied which considerably increases the reliability in evaluating test results. Since the reaction capillary has a downstream region in which the flow speed of the sample-reagents mixture is less than in the upstream region, larger agglomerations of latex particles can form without substantially reducing or even stopping the flow of the sample-reagents mixture through the reaction capillary. Larger agglomerations of latex particles also facilitate visual evaluation of the tests or manipulation of the test element in practice.

The transition between the upstream and downstream region of the reaction capillary can be stepwise, but a continuous transition is preferred. It particularly is preferred for the cross-sectional area (e.g., thickness and width) of the reaction capillary to increase in a continuous and consistent manner (e.g., linear increase over predetermined segments of the reaction capillary), or at least not decrease, in the direction of the sample-reagents mixture flow. Optionally, according to a preferred feature of the invention the test element comprises at least a pair of plate-like members which between them form a reaction capillary having a substantially rectangular cross-sectional configuration, the cross-sectional dimension of the reaction capillary in the thickness direction (i.e., spacing between the pair of plates) being smaller along the upstream region than along the downstream region. The capillary forces in the upstream region are therefore greater than in the downstream region, resulting in correspondingly different flow speeds through the reaction capillary. Tests have shown that maintenance within varied limits of a given transit time of the sample-reagents mixture through the reaction capillary is further assisted if, according to another preferred feature of the invention, the reaction capillary is substantially S-shaped, an intermediate region being provided between the upstream and downstream regions and having a capillary action which causes the sample-reagents mixture to flow at a speed which is equal to or less than the speed along the upstream region and/or equal to or greater than the speed along the downstream region. At the downstream end of the reaction capillary, optionally, there can be a region in which the sample-reagents mixture collects after flowing through the reaction capillary. This collection region facilitates observation and evaluation of the agglutination reaction.

The test element preferably is an assembly of particularly economically-manufactured injection-molded parts of suitable transparent plastics. This test element comprises, for example, injection-molded top and bottom plates which are joined together by welding or sticking (e.g., gluing) so as to form the reaction capillary between them. In a preferred method, the top and bottom plates are joined by ultrasonic welding to form a reaction capillary having the configuration according to the invention. In accordance with the preferred method, a weld web extending at least along the reaction capillary to be produced is formed on one of the plate-like members and a complementary weld groove is formed on the other plate-like member with a cross-sectional configuration such that the weld web is partly receivable therein. The plate-like members are brought together so that the web engages the groove, and ultrasonic energy is applied to the plate-like members so that the regions of the weld web in contact with the weld groove melt. The web joins the plate-like members by penetrating into the groove to a predetermined or preset depth for producing a reaction capillary having a dimension in the thickness direction which is smaller at the upstream end than at the downstream end. In this manner the dimension of the reaction capillary in the thickness direction can be exactly defined for obtaining the desired differential capillary effect. Ultrasonic welding is particularly economical.

The inventive test element can be used with immunological tests for detecting substances under search such as drugs, (particularly, drugs of abuse) habit-forming substances or the like in body fluids. In accordance with the invention for use in a competitive assay, a given quantity of the body fluid, an antibody reagent and a latex reagent are successively introduced into a receiving and mixing region of a test element, mixed together and the mixture is drawn into the reaction capillary. After the mixture has travelled through the reaction capillary the presence or absence of the substance under search is detected by visual observation of the presence or absence of agglutination-reaction products in the collecting region of the test element. The antibody, however, can be either part of the reagent or in the body fluid depending upon whether one is conducting a competitive or non-competitive assay, respectively.

BRIEF DESCRIPTION OF THE DRAWINGS

Preferred embodiments of the invention will now be explained in detail with reference to the drawings, in which:

FIG. 1 is a plan view of a test element for agglutination tests according to a preferred embodiment of the invention;

FIGS. 2–4 are sectional views along lines II—I, III—III and IV—IV in FIG. 1;

FIG. 5 is a sectional view along line V—V in FIG. 1, and

DETAILED DESCRIPTION OF THE PREFERRED EMBODIMENTS

Figure 6A:
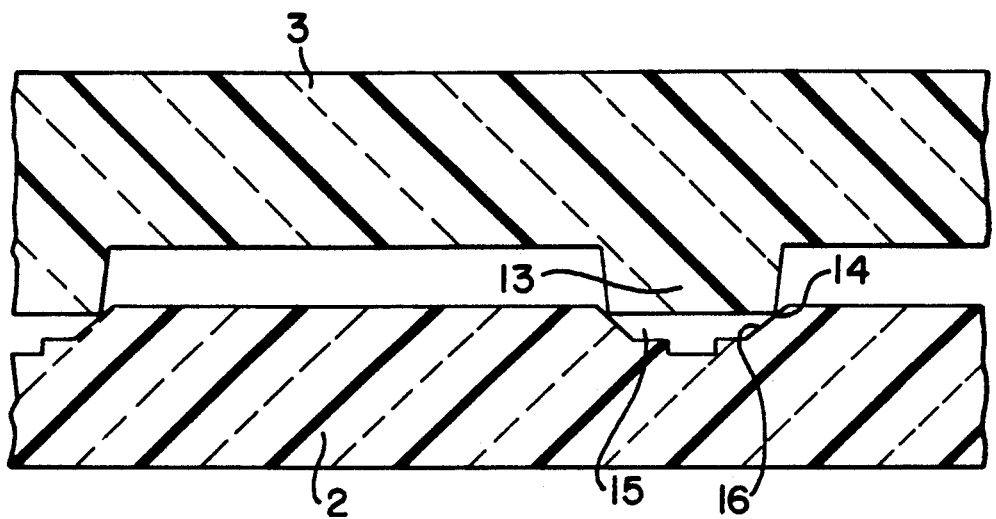
FIGS. 6A and 6B are larger-scale fragmentary cross-sectional views of the test element, showing the position of the plate-like members before and after welding.

The test element in a preferred embodiment of the invention is given the general reference number 1 and, as shown, comprises a pair of superposed top and bottom plate-like members 2, 3 which are firmly connected together (e.g., by sticking or welding) along web regions 13 described in detail hereinafter. Regions for receiving, moving and collecting a sample-reagents mixture for agglutination reactions are formed on one of members 2 or 3, more preferably the top member 3, and will likewise be described in detail hereinafter.

More particularly, a left-hand end portion (i.e., sample-reagent receiving portion) of the test element 1 in FIG. 1 is formed with an elongate recess which extends through the top plate-like member 3 and is covered at the bottom in fluid-tight manner by the bottom plate-like member 2, forming a region 7 for receiving and mixing the sample and the agglutination reagents. At the other or right-hand end portion (i.e., collection region) of test element 1, the underside of the top member 3 is formed with a substantially rectangular or square (or differently-shaped than the receiving region) recess which, in conjunction with member 2 which covers it, defines a chamber or region 8 in which the sample-reagents mixture can collect for further observation after travelling through a substantially S-shaped reaction capillary 4 extending between region 7 and 8.

The reaction capillary 4 is formed by a groove-like recess in the undersurface of the top member 3, covered in fluid-tight manner by the bottom member 2. Web 13 extends along the receiving and mixing region 7, the reaction capillary 4 and the collecting region 8, and thus constitutes a fluid-tight lateral boundary of these regions and of the reaction capillary (see FIGS. 2–4).

The reaction capillary 4 comprises a first or upstream capillary region or segment 9 which at one end (the upstream end 5) is in fluidic connection with the receiving and mixing region 7. The other end (downstream) of capillary region 9 is fluidically connected to an upstream end of a second or intermediate capillary region 11. The intermediate region 11 is likewise fluidically connected at its other end (downstream) to one end (the upstream end) of a third or downstream capillary region 10. The other or downstream end 6 of region 10 is in fluidic connection with the collecting region 8. The first, second and third capillary regions 9. 11, 10 preferably all have a substantially rectangular cross-section, as shown most clearly in FIG. 5, and preferably extend parallel to one another; the capillary regions 9 and 11, respectively 11 and 10 being in fluidic communication at their ends preferably via perpendicularly positioned capillaries or elbows.

In the embodiment shown, the dimension of the upstream and intermediate capillary regions 9, 11 in the width direction (i.e., looking along the capillary, the distance between the side walls) is substantially equal to and less than the dimension in the width direction of the downstream capillary region 10. Of course, the invention is not restricted to the aforementioned cross-sectional configuration or width dimension of the reaction capillary. In the thickness direction, (i.e., in the direction at right angles to the plane of FIG. 1 (note the distance between members 2 and 3 in FIGS. 2-4), there is a difference at least between the upstream or first region 9 and the downstream or third region 10. More particularly the thickness of the downstream region 10 is greater than that of the upstream region 9. The intermediate region 11 can have a thickness between that of the upstream region 9 and the downstream region 10. In the preferred embodiment any given point downstream has a cross-sectional area greater than or equal to (but not less than) any point upstream of such given point.

Owing to the difference in thickness between the capillary regions 9, 10 and 11, there are differences in the capillary forces therein, assuming that the other capillary influences are constant, and more particularly the capillary force in the upstream region 9 is greater than in the downstream region 10. The capillary forces in the intermediate region 11 can be adjusted, by suitably varying the thickness of region 11, so as to be equal to or less than the capillary forces in the upstream region 9 and/or equal to or greater than in the downstream region 10.

As shown more particularly in FIGS. 2-4, the thickness dimension along the capillary regions 9, 10, 11 is not constant from the upstream to the downstream ends, but alters, preferably continuously or stepwise if required. The thickness dimension at the upstream ends of the capillary regions is in each case less than at the downstream ends thereof. Preferably each capillary region 9, 10 11 of the reaction capillary 4 has a substantiallY conical or wedge-shaped cross-sectional configuration in the lengthwise (along flow) direction. On the other hand, as shown, the thickness dimension of the collecting region 8 at the downstream end 6 of capillary 4 can be constant. Reference 12 in FIG. 1 denotes bores for ventilating the collecting region 8.

As a result of the different capillary forces provided by the differences in cross-section area, more preferably thickness, along the reaction capillary 4, the flow speed of the sample-reagents mixture is greater along the upstream capillary region 9 than along the downstream capillary region 10. The conditions along the intermediate capillary region 11 can be transitional. The greater capillary forces in the upstream region 9 have a strong, continuous attracting effect on the reagents in the receiving and mixing region 7 and draw them into capillary 4. With the higher flow speed along this region 9, the sample-reagents mixture is "pumped" into the downstream capillary regions 10 and 11, where the capillary effect is less. As a result, a positive flow of sample-reagents mixture is produced and maintained along the entire reaction capillary 4 and into the collecting region 8.

In principle, the dimensions of capillary 4 in the thickness direction from the upstream end 5 to the downstream end 6 should be adapted to the respective sample-reagents mixture under investigation. Depending on the mixture, the thickness can be between about 1 and 100 $\mu$m at the upstream end 5 and between about 5 and 500 $\mu$m at the downstream end 6. Preferably the reaction capillary is between about 50 and 100 $\mu$m thick at the upstream end and between about 200 and 300 $\mu$m at the downstream end 6.

The thickness dimensions can be different, and the thickness of the reaction capillary along its entire length need not always change from a thinner region to a thicker region in the flow direction. In a preferred embodiment, however, the cross-sectional area, particularly increases continuously and constantly (e.g. linearly) from the upstream end to the downstream end and over each of the capillary regions 9, 10 and 11. Alternatively, if required, there can also be intermediate region(s) giving a lower or higher flow speed.

Also, the capillary action or flow speed along the reaction capillary can be influenced or changed by factors other than the cross-sectional configuration. Without attempting to be all inclusiveness, these factors include the surface quality, particularly the roughness of the capillary walls, the material of which the test element is made, more particularly admixtures such as additives or moisture therein, internal stresses and orientations of the material resulting from manufacturing the test element, and the like.

The test element is preferably an assembly of injection-molded parts made of a suitable transparent plastic such as polycarbonate, polystyrene, polymethylmethacrylate or acrylonitrilebutadiene-styrene based resins. Polymethylmethacrylate (PMMA) is particularly preferred owing to its good optical properties, good weldability and ease of processing by injection molding. If required, of course, other materials including inorganic materials such as glass can be used. The addition of anti-static materials to the resins also is contemplated. Applicants additionally contemplate the use of carbon black as an additive to the plastic for reducing static loading.

When Polymethylmethacrylate (PMMA) is used, one of the following additives can for instance be used a) Carbon Black pigment produced by the Degussa Company, Hanau, West-Germany, and sold under the trade name Masterbatch CB 51. This additive is added to a percentage of 3-5%.

b) An antistatic material produced by ICI and sold under the trade name ATMER 129, which comprises glycerol monostereate (90%) and some glycerol distereate. This additive is added to percentage of e.g. 0, 125%, 0,25% or 0,5%.

c) An antistatic material produced by the Lanko Company and sold under the trade name LANKO-STAT JP, which comprises lauric acid diethanolamine. This additive is added e.g. to a percentage of 0,5%.

Also instead of a reaction capillary 4 comprising substantially parallel capillary regions, the reaction capillary can extend in a straight line or can have any other desired configuration, e.g. a spiral arrangement of capillary regions. An intermediate capillary region 11 is not obligatory. Moreover, in this invention it is contemplated that the sample-reagents mixture may include the antibody for a competitive assay analysis but need not for a non-competitive assay analysis. In the latter assay, the antibody is in the boyd fluid (e.g., AIDS testing).

Illustratively, a test element of the aforementioned kind can be used for an agglutination test as follows. A given quantity of fluid under investigation (e.g., urine or blood from a person) can be introduced into the receiving and mixing region 7 of test element 1 followed in succession by given quantities (e.g. one drop each) of a reagent containing antibodies, a buffer reagent and a reagent comprising latex particles coated with a substance under search or a metabolite thereof, followed by gentle mixing in the receiving and mixing region 7. In a competitive assay test, the reagent also contains antibodies. Owing to the strong capillary effect in the upstream capillary region 9, the mixture is automatically sucked through opening 5 into capillary 4 and "pumped" into the downstream capillary regions 10 and 11.

The sample-reagents mixture is kept in an active state for agglutination simply by flowing along the reaction capillary, so that no external forces on the test element are needed for keeping the mixture in motion. Visible agglutinations are formed mainly along the downstream capillary region 10 and can be efficiently observed and evaluated visually, particularly in the collecting region 8. Owing to the pumping effect of the upstream capillary region 9, the time for the sample-reagents mixture to flow from the upstream end 5 to the downstream end 6 of capillary 4 or completely fill the collecting region 8 is accurately reproducible and can be optimized for maximum sensitivity, particularly with respect to the particular sample-reagents mixture The test element is particularly suitable for detecting cocaine metabolites. To this end a latex particle coated with, for example, a derivative of benzoyl ecgonine is used together with a monoclonal antibody against a benzoyl ecgonine immunogen and urine as the body fluid. The invention, however, is not restricted to this use.

The following Example illustrates the use of the test element in accordance with the invention.

EXAMPLE

A test element as per FIG. 1 was made from a Polymethylmetacrylate plastics (PMMA), e.g. PMMA obtainable under the trade name Diacon The test element is manufactured by injection molding and ultrasonic welding by a method described in detail hereinafter. The dimensions of the reaction capillary were:

Length of capillary regions 9,11,10: about 50 mm in each case; width of upstream and intermediate capillary regions 9,11: about 2 mm in each case; width of downstream capillary region 10: 3 mm; thickness of capillary regions, measured at upstream and downstream ends respectively: upstream capillary region 9: 80 and 130 $\mu$m, intermediate capillary region 11: 130 and 170 $\mu$m, downstream capillary region 10: 200 and 240 $\mu$m; thickness of collecting region 8: 240 $\mu$m.

A sample-reagents mixture of the aforementioned kind for detecting substances under search in urine was supplied to the receiving and mixing region 7 of the test element and a measurement was made of the time for the sample-reagents mixture to flow along the individual capillary regions until the collecting region 8 was full. The following average times were measured: 12 seconds for the upstream capillary region 9, 26 seconds for the intermediate region 11 and 140 seconds for the downstream region 10 including the collecting region 8.

The total time for the agglutination reaction was about 3 minutes, which is considered as optimal for the reagent mixture in question, as regards sensitivity of evaluation. The coefficient of variation ([standard deviation/mean time]$\times$100) for any set of measurements is preferably not more than 10%.

Figure 6B:
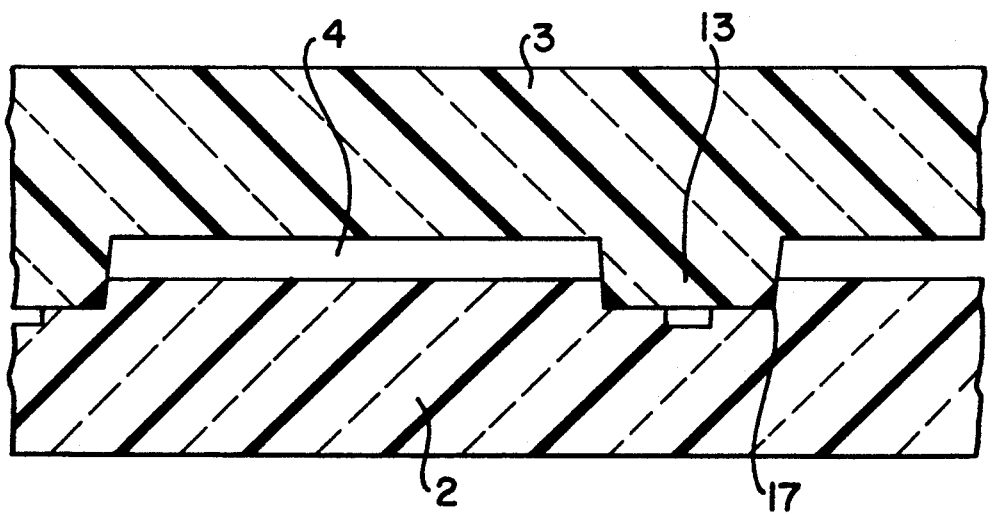

The following is a description, with reference to FIGS. 6A and 6B, of a preferred method for joining plate-like members 2, 3 made by injection-molding from a plastics, more particularly PMMA. FIGS. 6A and 6B show the plate-like members 2, 3 in the state respectively before and after joining by ultrasonic welding. As initially described, a continuous (or discontinuous if required) web 13 extends peripherally along regions 7 and 8 and at least along the reaction capillary 4. In the starting position in FIG. 6A, web 13 has a substantially rectangular or slightly trapezoidal cross-section. The web 13 in the top member 3 corresponds to a complementary groove 15 in the bottom member 2. The groove 15 has a cross-sectional configuration which, as shown, can only partly receive the web 13. More particularly, groove 15 has a substantially frusto-conical, inwardly tapering cross-section, so that the sides 14 of web 13 can engage the conical sides 16 of groove 15 at an intermediate place. If ultrasonic energy is applied to members 2, 3 in this initial position, in a manner known to a person skilled in the art, the regions of web 13 engaging the sides 16 of groove 15 melt, as shown at 17 in FIG. 6B.

As a result of the welding pressure exerted on members 2 and 3, web 13 is pushed further into groove 15 until the end face of web 13 abuts the base of groove 15. At this stage, the thickness dimension of the reaction capillary 4 and the collecting region 8 between the adjacent web regions is fixed, and also these regions are sealed in fluid-tight manner from the exterior and the plate-like members 2 and 3 are firmly joined. The differences in thickness of capillary 4 along its length can be obtained either by suitable shaping, more particularly via the depth of those parts of the surface of the top and/or bottom plate-like member forming the reaction capillary, or alternatively, a certain part of the area can be injected so as to have a constant depth, but during welding the members 2, 3 can be held in an oblique starting position (not shown) relative to one another. The result is that a part (the left-hand part in FIG. 1) of web 13 occupies a different position in the associated groove 15 from the other or right-hand part of the web. Under these conditions, if ultrasonic energy is applied to members 2 and 3, the welding pressure pushes the left-hand part of the web more deeply into groove 15 than the right-hand part, resulting in corresponding differences in the cross-section of capillary 4. Of course, the weld web and groove can be disposed in the opposite manner, e.g. the web on the bottom member and the groove on the top member.

The invention has been described with particular reference to a preferred embodiment. Of course the invention is not restricted thereto. More particularly the inventive method of forming an agglutination capillary can be applied to test equipment of any other kind. Also, the differential capillary effect of the upstream and downstream regions of the reaction capillary can be obtained not only by differential thickness but in general by varying the cross-sectional dimensions of the capillary regions, particularly to increase linearly in the direction of the sample-reagents mixtures flow. The term "reaction capillary" includes even a very small or non-existent capillary effect in the downstream region.

I claim:

1. A test element for an agglutination test of a sample-reagent mixture, comprising at least one pair of plate members defining therebetween a reaction capillary having a predetermined thickness for the sample-reagent mixture to flow through the capillary, the reaction capillary having an input end and an output end, the input end of the reaction capillary being fluidically connected to a zone for receiving and mixing the sample with the reagent, wherein:

the reaction capillary has a substantially rectangular cross-sectional configuration in a direction perpendicular to the flow of the sample-reagent mixture, the reaction capillary further has an upstream region with a thickness at the input end of between about 50 and about 100 μm and a downstream region with a thickness at the output end of between about 200 and about 300 μm, the thickness of the reaction capillary increasing from the upstream region toward the downstream region, and the increase in the reaction capillary thickness is substantially continuous and linear over the length of each region.

2. The test element of claim 1, wherein the smallest reaction capillary thickness in the downstream region is at least as large as the largest reaction capillary thickness in the upstream region.

3. The test element of claim 1, wherein the reaction capillary has an intermediate region disposed between the upstream region and the downstream region and fluidically communicating with said upstream and downstream regions, the intermediate region being of such dimensions so as to provide a capillary effect which causes the sample-reagent mixture to flow at a speed which is equal to or less than the speed along the upstream region.

4. The test element of claim 1, wherein the reaction capillary has an intermediate region disposed between the upstream region and the downstream region and fluidically communicating with said upstream and downstream regions, the intermediate region being of such dimensions so as to provide a capillary effect which causes the sample-reagent mixture to flow at a speed which is equal to or greater than the speed along the downstream region.

5. The test element of claim 1, wherein the reaction capillary has an intermediate region disposed between the upstream region and the downstream region and fluidically communicating with said upstream and downstream regions, the intermediate region being of such dimensions so as to provide a capillary effect which causes the sample-reagent mixture to flow at a speed which is equal to or less than the speed along the upstream region and equal to or greater than the speed along the downstream region.

6. The test element of claim 5, wherein the reaction capillary has a substantially S-shaped configuration along the direction of flow of the sample-reagent mixture.

7. The test element of claim 1, wherein each plate member of said at least on pair of plate members has a predetermined length, and the reaction capillary has a length which is greater than the length of one of said plate members.

8. The test element of claim 7, wherein the reaction capillary has a substantially S-shaped configuration along the direction of flow of the sample-reagent mixture.

9. The test element of claim 7, further comprising a collection region fluidically connected to the output end of the reaction capillary.

10. The test element of claim 9, wherein at least one of the plate members is made from transparent plastics.

11. A test element for use in detecting the agglutination of a sample-reagent mixture, comprising a top plate member and a bottom plate member secured together, at least one of said plate members defining a channel having a predetermined thickness and configured to form a reaction capillary between the plate members for passing the sample-reagent mixture therethrough, the reaction capillary having an input end and an output end, the reaction capillary having an upstream region with a thickness at the input end of between about 50 and about 100 μm and with means defining an aperture at the input end for receiving the sample-reagent mixture, and a downstream region fluidically communicating with the upstream region and with a thickness at the output end of between about 200 and about 300 μm, wherein the reaction capillary has a substantially rectangular cross-sectional configuration in a direction perpendicular to the flow of the sample-reagent mixture, the thickness of the reaction capillary increases in a direction from the upstream region toward the downstream region, and the increase of the reaction capillary thickness is substantially continuous and linear over the length of each region.

12. The test element of claim 11, wherein the top plate member has means defining an aperture forming thereunder with the bottom member a chamber for receiving and mixing the sample and at least one reagent to form the sample-reagent mixture, the chamber fluidically communicating with the aperture in the upstream region of the reaction capillary.

13. The test element of claim 12, wherein the upstream and downstream regions have substantially equal lengths.

14. The test element of claim 12, wherein the capillary further comprises an intermediate region having ends which fluidically communicate with the upstream region and downstream region, respectively.

15. The test element of claim 12, further comprising a collecting chamber fluidically connected to the output end of the reaction capillary.

16. The test element of claim 12, wherein the top and bottom plate members each have predetermined lengths and the reaction capillary has a length which is greater than the length of at least one of said top and bottom plate members.

17. The test element of claim 16 wherein the reaction capillary has a substantially S-shaped configuration along the direction of flow of the sample-reagent mixture.

* * * * *